(12) United States Patent
Saxena et al.

(10) Patent No.: US 9,890,234 B2
(45) Date of Patent: *Feb. 13, 2018

(54) ORGANO-MODIFIED SILICONE POLYMERS AND HYDROGELS COMPRISING THE SAME

(71) Applicants: Anubhav Saxena, Bangalore (IN); Sandeep Shashikant Naik, Bangalore (IN); Monjit Phukan, Bangalore (IN); Shreedhar Bhat, Bangalore (IN)

(72) Inventors: Anubhav Saxena, Bangalore (IN); Sandeep Shashikant Naik, Bangalore (IN); Monjit Phukan, Bangalore (IN); Shreedhar Bhat, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/492,646

(22) Filed: Sep. 22, 2014

(65) Prior Publication Data

US 2015/0011671 A1 Jan. 8, 2015

Related U.S. Application Data

(63) Continuation of application No. PCT/US2013/029302, filed on Mar. 6, 2013.

(60) Provisional application No. 61/614,262, filed on Mar. 22, 2012.

(51) Int. Cl.
| | |
|---|---|
| *C08F 283/12* | (2006.01) |
| *C08L 83/14* | (2006.01) |
| *G02B 1/04* | (2006.01) |
| *C08G 77/48* | (2006.01) |
| *C08G 77/50* | (2006.01) |
| *C08G 77/38* | (2006.01) |
| *C08K 3/20* | (2006.01) |
| *C07F 7/18* | (2006.01) |
| *C07F 7/21* | (2006.01) |
| *C08F 230/08* | (2006.01) |

(52) U.S. Cl.
CPC ........ *C08F 283/124* (2013.01); *C07F 7/1852* (2013.01); *C07F 7/1856* (2013.01); *C07F 7/21* (2013.01); *C08G 77/38* (2013.01); *C08G 77/48* (2013.01); *C08G 77/50* (2013.01); *C08K 3/20* (2013.01); *C08L 83/14* (2013.01); *G02B 1/043* (2013.01); *C08F 230/08* (2013.01); *C08G 2210/00* (2013.01); *G02B 2207/109* (2013.01)

(58) Field of Classification Search
None
See application file for complete search history.

(56) References Cited

U.S. PATENT DOCUMENTS

| | | | |
|---|---|---|---|
| 3,408,429 A | 10/1968 | Wichterle | |
| 3,496,254 A | 2/1970 | Wichterle | |
| 4,084,459 A | 4/1978 | Clark | |
| 4,197,266 A | 4/1980 | Clark et al. | |
| 4,260,725 A | 4/1981 | Keogh et al. | |
| 4,433,125 A * | 2/1984 | Ichinohe | C08F 230/08 351/159.33 |
| 4,450,264 A * | 5/1984 | Cho | C07F 7/0852 526/279 |
| 5,352,714 A | 10/1994 | Lai et al. | |
| 5,981,669 A | 11/1999 | Valint, Jr. et al. | |
| 5,998,498 A | 12/1999 | Vanderlaan et al. | |
| 6,013,711 A | 1/2000 | Lewis et al. | |
| 6,207,782 B1 | 3/2001 | Czech et al. | |
| 6,867,245 B2 | 3/2005 | Iwata et al. | |
| 7,268,189 B2 | 9/2007 | Muller et al. | |
| 2008/0231798 A1* | 9/2008 | Zhou | C08F 283/12 351/159.33 |
| 2009/0141234 A1* | 6/2009 | Blackwell | C08F 220/02 351/159.33 |
| 2009/0143499 A1 | 6/2009 | Chang et al. | |
| 2009/0192234 A1 | 7/2009 | Saxena et al. | |
| 2010/0296049 A1 | 11/2010 | Justynska et al. | |
| 2010/0298446 A1* | 11/2010 | Chang | C08F 230/08 514/772.4 |
| 2011/0166248 A1 | 7/2011 | Hsu et al. | |
| 2011/0181833 A1* | 7/2011 | Guyer | C07F 7/0852 351/159.33 |

(Continued)

FOREIGN PATENT DOCUMENTS

| | | |
|---|---|---|
| EP | 0632329 B1 | 1/1995 |
| WO | 199415980 A1 | 7/1994 |
| WO | 2008116131 A2 | 9/2008 |
| WO | 2009094221 A1 | 7/2009 |
| WO | 2010038242 A2 | 4/2010 |
| WO | 2013029316 A1 | 3/2013 |
| WO | 2013142052 A2 | 9/2013 |

OTHER PUBLICATIONS

International Search Report and Written Opinion of the International Searching Authority, PCT/US2013/029302, Momentive Performance Materials, Inc., May 8, 2013.

(Continued)

*Primary Examiner* — Peter A Salamon

(74) *Attorney, Agent, or Firm* — McDonald Hopkin LLC; Joseph Ostroff

(57) ABSTRACT

A hydrophilic silicone polymer composition suitable for use in producing hydrogel polymer films disclosed. In one aspect, a hydrophilic silicone monomer is of the Formula 1:

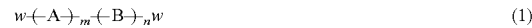

where A is a divalent block comprising a silicone-containing pendant group. In one embodiment, the silicone-containing pendant group comprises polyalkylene oxide groups. The structure of the polymer can be controlled and tuned to provide a material with excellent wettability and oxygen permeability. The polymers are suitable for use in a variety of applications including in providing a film for forming contact lenses.

16 Claims, No Drawings

(56) References Cited

U.S. PATENT DOCUMENTS

| | | | | |
|---|---|---|---|---|
| 2012/0046382 A1* | 2/2012 | Zhou | ................... | C08F 283/12 523/107 |
| 2012/0244088 A1* | 9/2012 | Saxena | ................ | A61K 47/34 424/49 |
| 2015/0011671 A1* | 1/2015 | Saxena | ................ | C08L 83/14 523/107 |
| 2015/0011788 A1* | 1/2015 | Saxena | ................ | C08L 83/14 556/437 |

OTHER PUBLICATIONS

International Preliminary Report on Patentability, PCT/US2013/029302, Momentive Performance Materials, Inc., May 12, 2015.
International Search Report and Written Opinion of the International Searching Authority, PCT/US2013/029316, Momentive Performance Materials, Inc., May 8, 2013.
International Preliminary Report on Patentability, PCT/US2013/029316, Momentive Performance Materials, Inc., May 5, 2015.
Extended European Search Report for Application No. 13764947.1, dated Mar. 9, 2016.
Extended European Search Report for Application 113764947.1-1301, PCT/US2013029302, dated Mar. 9, 2016, 8 pgs., European Patent Office.
Extended European Search Report for Application 13763479.6-1301, PCT/US2013029316, dated Jun. 14, 2016, 8 pgs., European Patent Office.
United States Office Action for U.S. Appl. No. 14/492,378, dated Jun. 23, 2016.
Japan Patent Office (JPO), Notification of Reasons for Rejection for Patent Application No. 2015-501,698, drafted Nov. 10, 2016, dated Nov. 15, 2016, Third Patent Examination Department, Japan.
State Intellectual Property Office of People's Republic of China, Notification of First Office Action for Application No. 2013800224460.1, report issue date Aug. 12, 2016, China.

* cited by examiner

ORGANO-MODIFIED SILICONE POLYMERS AND HYDROGELS COMPRISING THE SAME

CROSS REFERENCE TO RELATED APPLICATIONS

This application is a continuation of International Patent Application No. PCT/US2013/029302, entitled "Organo-Modified Silicone Polymers and Hydrogels Comprising the Same", filed on Mar. 6, 2013, which claims the priority benefit of U.S. Provisional Patent Application No. 61/614,262, entitled "Organo-Modified Silicone Polymers and Hydrogels Comprising the Same", filed on Mar. 22, 2012, each of which are hereby incorporated in their entirety by reference.

FIELD OF THE INVENTION

The present invention relates to hydrogel compositions comprising organo-modified silicone-containing polymers. The present invention relates, in one aspect, to organosiloxane amphiphilic polymers and compositions comprising the same. The polymers are useful as simple additives or as pre-polymers in variety of compositions and formulations including, for example, personal care and hydrogel compositions and films suitable for producing biomedical products including contact lenses.

BACKGROUND

Organo-modified silicone polymers are used in multitude of applications such as healthcare, personal care, home care, coatings, agricultural compositions etc. The presence of enough organic content can bring significant changes in properties associated with bare silicones. The common approach to synthesizing silicone-organic polymer is bulk polymerization of silicone monomers/macromers with organic monomers/macromers. This leads to randomized structure with an uncontrolled degree of cross-linking which hampers reproducibility in synthesis and thereby the final properties. There is a need to develop an approach to carefully design and build silicone-organic polymer with well-defined structure, controlled composition and tunable structure-property relationship. These polymers can have terminal or pendant reactive groups for further polymerization i.e. pre-polymer, which make them useful in reactive composition such as copolymers, hydrogels, coating, emulsions/latex etc.

Curable silicone-hydrogel formulations are used to make extended wear soft contact lenses due to their relatively high oxygen permeability, flexibility, comfort, and reduced corneal complications. Conventional hydrogel materials (e.g. 2-hydroxyethyl methacrylate, HEMA) by themselves have poor oxygen permeability and they transport oxygen to the eye through the absorbed water molecules. Water has low oxygen permeability, also called the Dk value, which may be expressed in Barrer, wherein 1 Barrer=$10^{-11}$ (cm$^3$ O$_2$) cm cm$^{-2}$ s$^{-1}$ mmHg$^{-1}$ where "cm$^3$ O$_2$" is at a quantity of oxygen at standard temperature and pressure and where "cm" represents the thickness of the material and "cm$^{-2}$" is the reciprocal of the surface area of that material. The Dk of water is 80 Barrer. Upon exposure to atmospheric air for long periods, these lenses are slowly dehydrated and the amount of oxygen transported to the cornea is reduced. Eye irritation, redness and other corneal complications can result and hence restrict use of the lenses to limited periods of wear.

Silicone-hydrogel materials and films for contact lenses are popular for their high oxygen permeability, flexibility and comfort. Silicone material, however have poor wettability, and hence several methods have been developed to improve the water content of these hydrogel formulations. This includes adding hydrophilic monomers to the hydrogel formulations. But this causes incompatibility between silicone and organic monomers and leads to phase separation.

A possible solution to this problem is to make the silicone monomer inherently hydrophilic by incorporating hydrophilic units in the monomer. One approach to provide hydrophilic silicone monomers is to polymerize the organo-modified silicone monomer with organic monomers in the presence of a cross-linker. Examples of prior attempts of providing hydrophilicity include those described in U.S. Pat. Nos. 4,260,725; 5,352,714; 5,998,498; 6,867,245; 6,013,711; and 6,207,782. This approach leads to a large number of unreacted monomers due to unregulated viscosity build-up that requires extracting the leachable monomers from the matrix by water-isopropanol solvent mixtures, which leads to increased processing costs. Further, the silicone hydrogel formulations made by these methods still fail to exhibit significant wettability. To overcome this, more hydrophilic monomers or internal wetting agents are added to the hydrogel compositions, but this compromises oxygen permeability. Alternatively, a secondary treatment such as "plasma oxidation" can be used, but this treatment is expensive.

The use of pre-polymers is one approach to providing silicone monomers with improved hydrophilicity and oxygen permeability that can be cured in a controlled fashion so as to reduce leachable monomers/oligomers, processing cost and toxicity. The pre-polymer approach ties up the silicone chemistry with polymerization techniques to synthesize silicone-organic polymers with a well-defined structure and controlled composition. Significantly high hydrophilicity can be achieved without compromising oxygen permeability. Further, the polymer composition can be tunable such that it can be tailored to provide particular properties depending on the intended use. These polymers are further functionalized with a reactive group and introduced into a curable composition. This concept brings in reproducibility and increases the purity of the final materials.

Some prior attempts to provide suitable pre-polymers include the approach of U.S. Pat. No. 7,268,189, which describes polysiloxane based cross-linkers used in combination with a hydrophilic monomer in the presence of a chain transfer agent to yield an amphiphilic pre-polymer. U.S. Pat. No. 5,981,669 relates to the synthesis of a mono-functional pre-polymer by the free-radical polymerization of a silicone monomer and a hydrophilic monomer in the presence of a chain transfer agent. These pre-polymers were then introduced into formulations with bi-functional macromer which may be composed of silicone. U.S. Patent Publication Nos. 2011/0166248A1 and 2008/0231798 describe block copolymers of silicone-containing monomers and hydrophilic monomers to yield a pre-polymer. U.S. Patent Publication No. 2010/0298446 reports functionalization of polysiloxane blocks to act as a macro initiator for polymerizing a hydrophilic monomer via. atom transfer radical polymerization (ATRP). This technique yields bi- or tetra-functional pre-polymer. U.S. Patent Publication No. 2010/0296049 describes a reversible addition fragmentation chain transfer (RAFT) technique for polymerizing a mixture of a bi-functional polysiloxane polymer and an organic monomer. U.S. Patent Publication No. 2009/0143499 describes, a pre-polymer made of polysiloxane blocks, poly (oxyalkylene) blocks, and cross-linkable groups.

Conventionally, silicone-hydrogels are made by polymerizing the acrylate or methacrylate functionalized silicone monomer with hydrogel (hydrophilic) monomers, such as 2-hydroxyethyl methacrylate (HEMA), N-vinylpyrrolidone (NVP) and other monomers such as methyl methacrylic acid (MMA), N,N-dimethylacrylamide (DMA), etc., in the presence of cross-linker and free radical or photoinitiators. Cross-linking agents generally have two or more reactive functional groups at different sites of the molecule. Typically, these sites contain polymerizable ethylenic unsaturation groups. During curing, they form a covalent bond with two different polymer chains and form a stable three-dimensional network to improve the strength of the polymer. Cross-linking agents conventionally used in contact lenses include ethylene glycol dimethacrylate and trimethyloylpropane trimethacrylate (about 0.1 to 2 wt. %). Other useful cross-linking agents include diethyleneglycol dimethacrylate, bisphenol A dimethacrylate, diglycidyl bisphenol A dimethacrylate and dimethacrylate-terminated polyethylene glycol and reactive linear polyether modified silicones.

Generally, silicone hydrogel contact lens materials are made using either hydrophobic mono-functional silicone monomer (such as TRIS) or multi-functional hydrophilic silicone monomer followed by secondary surface treatment. Mono-functional silicone monomers are preferred in the contact lens industry over multi-functional silicone monomers since the latter lead to increased rigidity of the lens made therefrom.

The state of this art for soft contact lenses, including the silicone-based materials described in the above mentioned patents, still possess major shortfalls like sub-optimal surface wettability and lipid deposition. There remains a need for hydrophilic silicone monomers with advantageous wettability and oxygen permeability that can be used to make contact lenses without the drawbacks and expensive surface treatments necessary with the silicone containing materials of the current state of art.

SUMMARY

The present invention discloses a composition comprising a silicone-containing polymer.

In one embodiment, the present invention provides a pre-polymer comprising a silicone monomer having polyether groups as a hydrophilic block that make the pre-polymer and thereby the hydrogel according to the present invention more hydrophilic.

The polymer can be formed by homopolymerization of a silicone-containing monomer and or by block polymerization of the silicone-containing monomer with other monomers in a sequential or random manner. The polymer can be formed by polymerizing such monomers via free radical polymerization (FRP), atom transfer radical polymerization (ATRP), or reversible addition fragmentation chain transfer (RAFT). This can allow for the controlled synthesis of a polymer having a well-defined architecture. This can also allow for the siloxane blocks or polyether blocks to be controlled or varied, which allows the oxygen permeability and hydrophilicity of the pre-polymer to be controlled or tuned. This process also avoids problems associated with prior silicone polyethers formed by hydrosilylation of hydrogen containing siloxanes with polyethers containing primary olefinic groups. In particular, the present method avoids the possible isomerization of the double bond in the olefin group, which can make it ineffective for reaction.

In one embodiment, the present invention provides a hydrogel composition comprising a siloxane amphiphilic polymer of the Formula 1:

$$w\text{-}(\text{-}A\text{-})_m\text{-}(\text{-}B\text{-})_n\text{-}w \qquad (1)$$

where the divalent block A comprises a silicone-containing pendant group. In one embodiment, the silicone-containing pendant group is a polyether group containing alkylene oxide units and siloxane units.

In one embodiment, the hydrogel composition comprises (a) a silicone pre-polymer in accordance with aspects of the invention, (b) a free-radical polymerizable organic monomer, (c) an initiator, and (d) optionally a cross-linker. Silicone hydrogel films produced with these macromers offer improved surface wettability, water absorption, contact angle, oxygen permeability, curing characteristics and mechanical properties in comparison to silicone-hydrogel films prepared from monomers having linear alkyl linking groups, such as those already disclosed in the prior art for contact lens applications.

The compositions according to current invention can be homopolymers and copolymers that may be used to form films, emulsions, or latex particles. Such materials may further be used in formulations for a wide variety of applications. In one embodiment, the compositions are useful to make water-absorbing, oxygen-permeable silicone-hydrogel films that can be fashioned into extended wear soft contact lens. In one embodiment, the homopolymer, copolymer, emulsion, and latex particles according to the current invention can also be used as ingredients in personal care formulation including skin care, hair care, and nail care, such as lipsticks, mascaras, foundations, lotions, creams, shampoos, conditioners and nail polishes, to improve their ware, tactile properties and ease of application. In another embodiment they can be used in textile and fiber treatment applications to impart smooth, soft feel and wettability to both natural and synthetic fibers. In still another embodiment, the homopolymer, copolymer, emulsion and latex particles can be incorporated into fertilizers, pesticides, adhesives, or coating formulations for metal, plastic, wood and paper, such as varnishes, latex paints and roofing compositions.

These and other aspects of the invention can be further understood with reference to the following detailed description.

DETAILED DESCRIPTION

In accordance with aspects of the present invention, a hydrogel composition comprising hydrophilic silicone macromers having a free radical polymerization-effective hydrophilic group and useful for preparing water-absorbing silicone hydrogel films that can be used in contact lens applications are described. Silicone hydrogel films obtained with these monomers show excellent wettability, oxygen permeability and desirable modulus in comparison to previously known films.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

A "macromer" refers to a medium and high molecular weight compound that can comprise one or more functional groups capable of being polymerized, cross-linked, or both. A "monomer" refers to a relatively low molecular weight compound that is polymerizable.

A "hydrophilic" substance (e.g., hydrophilic monomer, hydrophilic macromer, hydrophilic polymer, etc.) is one that is water-loving, has an affinity for water, is capable of absorbing water, etc. A hydrophilic substance may be soluble or insoluble (e.g., substantially insoluble) in water. A hydrophilic substance can, in one embodiment, contain both hydrophilic and hydrophobic potions, but the hydrophobic portions are present in relative amounts such that the substance or component is hydrophilic. In one embodiment, a hydrophilic substance can absorb at least 10 percent by weight water.

"Homopolymers" are polymers made from the same repeating macromer or monomer. "Copolymers" are polymers wherein the polymer contains at least two structurally different macromers, at least two structurally monomers, or at least one macromer and at least one monomer. Notations such as (meth)acrylate denote monomer with either acrylate or methacrylate functionality.

A "pre-polymer" is a reaction intermediate polymer of medium molecular weight having terminal or pendant polymerizable groups.

A "chain stopper" group is non-reactive group at the end of the polymer.

A "non-reactive polymer" is a polymer having no further polymerizable groups.

Hydrophilic Silicone Polymer

The present invention provides a hydrogel composition comprising a silicone-containing pre-polymer with the general structure:

  (1)

where m is a positive integer ranging from 2-100, and n is a positive integer 0-100. The divalent building block A has a general formula:

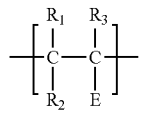

where $R_1$, $R_2$, and $R_3$ can be independently selected from hydrogen, monovalent radicals with 1 to 50 carbon-atoms, which may optionally contain heteroatoms such as O, N, P, halogens, or a combination of two or more thereof. E is a mono-valent group having a general structure of F-L-G, where F is a divalent linkage selected from alkyl, ester, ether, amine, amide, carbonate, carbamate, etc.; L is a divalent moiety chosen from a substituted and/or unsubstituted linear, branched, cyclic aliphatic hydrocarbon or aromatic hydrocarbon of 1-100 carbon atoms, which optionally contain one or more heteroatoms, and in one embodiment comprises a functionality such as an alcohol, an ether, an ester, an amide, an amine, a urea, a urethane, a cyano, a carbonate, a carbamate, a thio, or combinations of two or more thereof; and G is a siloxane unit having the general structure $M^1_a M^2_b D^1_c D^2_d T^1_e T^2_f Q_g$. G may be linear or branched where $M^1=R_5R_6R_7SiZ_{1/2}$, $M^2=R_8R_9R_{10}SiZ_{1/2}$, $D^1=R_{11}R_{12}SiZ_{2/2}$, $D^2=R_{13}R_{14}SiZ_{2/2}$, $T^1=R_{15}SiZ_{3/2}$, $T^2=R_{16}SiZ_{3/2}$, $Q=SiZ_{4/2}$; where $R_5$, $R_6$, $R_7$, $R_9$, $R_{10}$, $R_{11}$, $R_{12}$, $R_{14}$ and $R_{15}$ are independently chosen from a monovalent hydrocarbon radical having 1 to about 50 carbon atoms and may optionally contain heteroatoms; $R_8$, $R_{13}$, and $R_{16}$ are independently selected from a divalent residue from a non-isomerizable hydrosilylation effective terminal olefin with the general structure:

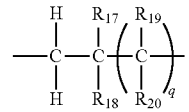

where $R_{18}$, $R_{19}$, and $R_{20}$ are independently selected from hydrogen and a hydrocarbon radical with 1 to 10 carbon-atoms that optionally contain a heteroatom; the integer q can be 0 to 10, and $R_{17}$ is a hydrocarbon radical with 1 to 5 carbon atoms or a hydrogen atom such that $R_{17}$ is hydrogen if q=0 and L is a cyclic residue. The subscripts a, c, e, and g can be zero or positive integer such that $0<a+b+c+d+e+f+g<500$. The subscripts b, d, and f can have values of 0 or 1 such that $b+d+f=1$. Z can be O or a $CH_2$ group subject to the limitation that the molecule contains an even number of $O_{1/2}$ and an even number of $(CH_2)_{1/2}$ groups, and the $O_{1/2}$ and the $(CH_2)_{1/2}$ groups both are all paired in the molecule.

The divalent radical B has the general formula:

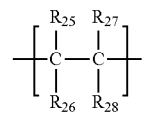

where, $R_{25}$, $R_{26}$, $R_{27}$, and $R_{28}$ can independently be selected from hydrogen, halogens, hydroxyl and hydrocarbon radicals comprising of aromatic, aliphatic, aralkyl moieties optionally having heteroatoms.

W can be selected from X or Y where, X stands for a free radical polymerizable group and Y stands for a chain stopper group. The polymer according to the present invention is termed as 'pre-polymer' when at least one of W is selected from X.

X is a polymerizable group under free radical polymerization conditions. Examples of suitable molecules for X are acrylate, acrylamide, methacrylate, methacrylamide, vinyl, allyl, methallyl, and internal olefinic bond containing molecules such as butenedioic acid, butenedioic esters or amides, itaconic acid, itaconic acid esters or amides, etc. In one embodiment, X is a polymerizable group having the general formula:

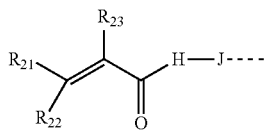

where, $R_{21}$, $R_{22}$, and $R_{23}$ can be selected from hydrogen or a monovalent hydrocarbon radical with 1 to 5 carbon atoms, which may optionally contain heteroatoms; H can be O or $NR_{24}$, where $R_{24}$ can be hydrogen or a monovalent hydrocarbon radical with 1-5 carbons; J is a divalent moiety chosen from a substituted or unsubstituted aliphatic or aromatic hydrocarbon having of 1-10 carbon atoms and may optionally contain a heteroatom.

Y can be independently selected from hydrogen, hydroxyl or a monovalent hydrocarbon radical having 1 to 10 carbon atoms, which may optionally contain heteroatoms.

In an exemplary embodiment of a pre-polymer, the E group in the divalent block A comprises a spacer L that is a hydrophilic residue chosen from a polyalkyleneoxide. In one embodiment, the polyalkylene oxide unit is chosen from —$CH_2CH_2O$—, —$CH_2CH(CH_3)O$—, —$CH_2CH_2CH_2O$—, and their analogues with up to 6 carbon atoms. In one embodiment, L is a cyclic hydrocarbon residue with the structure:

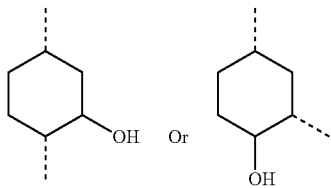

In another exemplary embodiment of a pre-polymer in accordance with aspects of the present invention, the E group in the divalent block A comprises a siloxane unit G comprising monovalent radicals $R_9$, $R_{10}$, $R_{11}$, $R_{13}$, $R_{14}$, $R_{15}$, $R_{16}$, $R_{18}$, and $R_{20}$ that are independently selected from hydrocarbon radicals such as methyl, ethyl, propyl, isopropyl, butyl, isobutyl, phenyl, naphthyl, aralkyl radicals with 8 to 20 carbon atoms, trifluoromethylpropyl etc.

In other exemplary embodiments of a pre-polymer according to aspects of the present invention, the monofunctional group E has a structure chosen from any of Formulas 2-9:

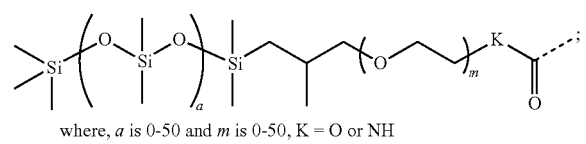

where, $a$ is 0-50 and $m$ is 0-50, K = O or NH

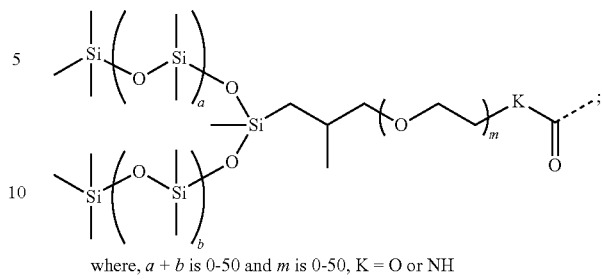

where, $a + b$ is 0-50 and $m$ is 0-50, K = O or NH

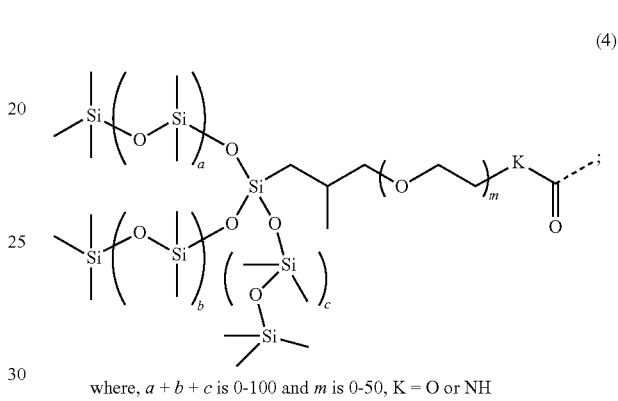

where, $a + b + c$ is 0-100 and $m$ is 0-50, K = O or NH

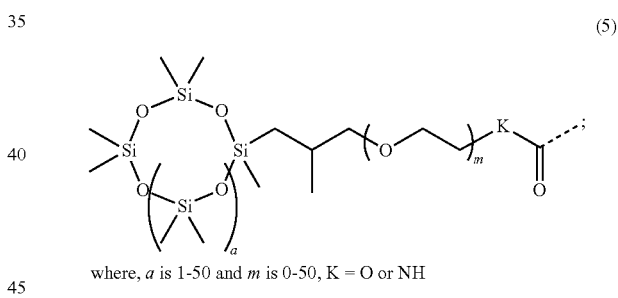

where, $a$ is 1-50 and $m$ is 0-50, K = O or NH

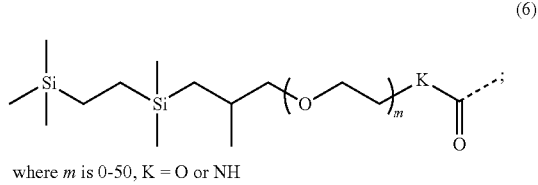

where $m$ is 0-50, K = O or NH

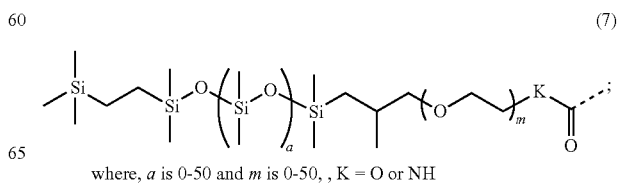

where, $a$ is 0-50 and $m$ is 0-50, , K = O or NH

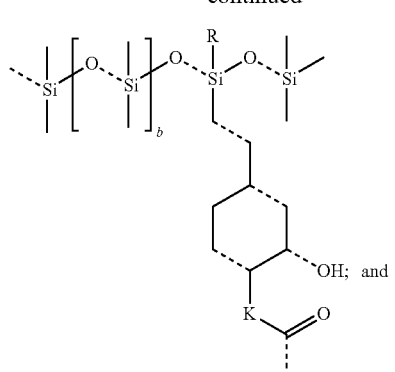

where K is O or NH, R is —CH$_3$ or —(OSi(CH$_3$)$_2$)$_n$, b is 0-100, and n + b is 0-100

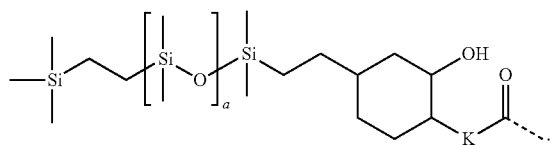

where K is O or NH, and a is 0-100

In yet another exemplary embodiment, the divalent radical component B of Formula 1 is chosen such that R$_{25}$ and R$_{26}$ are hydrogen, R$_{27}$ is chosen from hydrogen or a methyl radical, and R$_{28}$ is a part of ethylenically-unsaturated hydrophilic monomers such as, for example, 2-hydroxyethyl methacrylate, 2-hydroxy ethylacrylate, N,N-Dimethylacrylamide, N,N-dimethylmethacrylamide, N-hydroxyethyl acrylamide, N-vinyl-pyrrolidone, etc.

The hydrogel compositions can be used in a variety of applications and as part of a wide variety of formulations and compositions.

In one embodiment, a hydrogel composition comprises (a) a pre-polymer in accordance with aspects of the invention, (b) a free-radical polymerizable organic monomer, (c) an initiator, and (d) optionally a cross-linking agent.

The pre-polymer (a) can be a pre-polymer in accordance with aspects of the invention including, for example, pre-polymers having a structure of Formula 1.

The radical polymerizable effective monomers (b) can be an organic, silicone or organo-modified silicone molecules with one polymerizable group. Non-limiting examples of suitable polymerizable groups include acrylate, methacrylate, vinyl, allyl, methallyl, acrylamides, methacrylamides, N-vinyl lactam, N-vinyl amide, olefinically unsaturated hydrocarbons with carboxylic acids or esters, etc. More specific polymerizable groups include, but are not limited to, N,N-dimethylacrylamide, N,N-dimethylmethacrylamide, N-hydroxyethyl acrylamide, N-vinyl-pyrrolidone, N-vinylpyrrole, N-vinyl succinimide, alkyl vinyl ethers, 2-acrylamido glycolic acid, 2-hydroxyethyl methacrylate (HEMA), 2-hydroxy ethylacrylate (HEA), hydroxypropyl methacrylate, dimethylaminoethyl methacrylate, glycerol methacrylate, 2-ethyl hexyl acrylate, butyl acrylate, isooctyl acrylate, methyl methacrylate, lauryl acrylate, dodecyl acrylate, butyl acrylate, acrylic acid, maleic anhydride, vinyl acetate, allyl alcohol, acrylic acid, methacrylic acid, vinyl acetate, N-vinyl caprolactum, N-vinylformamide, N-vinyl acetamide, N-vinyl-N-methyl acetamide, N,N-vinyl-3-methyl caprolactum, N-vinyl imidazole, 2-acrylamidoglycolic acid, N-hydroxyethyl acrylamide, N-tertbutyl acrylamide, N-isopropylacrylamide, N-isopropylmethacrylamide, 2-acrylamido-2-methyl-1-propane sulfonic acid and its salts, (3-acrylamidopropyl)-trimethylammonium chloride, N,N-dimethylmethacrylamide, 3-acryloylamino-1-propanol, 2-acrylamidoglycolic acid, aminopropyl methacrylate, 3-tris (trimethylsiloxy)silylpropylmethacrylate (TRIS), bis-(trimethylsiloxy)methylsilylpropyl methacrylate, pentamethyldisiloxanepropylmethacrylate, pentamethyldisiloxanylmethylmethacrylate, tris(trimethylsiloxy)silylpropyloxyethylmethacrylate, tris(trimethylsiloxy)silylpropyloxyethyl methacrylate, tris(trimethylsiloxy)silylpropyl methacryloxyethylcarbamate, tris(trimethylsiloxy) silylpropyl glycerol. N-[tris(trimethylsiloxy)silylpropyl] methacrylamide, pentamethyldisiloxanyl methyl methacrylate, phenyltetramethyl disiloxanyl ethyl ethacrylate, 3-[tris(trimethylsiloxy)silyl]propyl vinyl carbamate, 3-[tris(trimethylsiloxy)silyl]propyl vinyl carbonate, 2-(acryloxyethyoxy)trimethylsilane, N-(3-acryloxy-2-hydroxypropyl)-3-aminopropyl triethoxysilane, (acryloxymethyl)phenethyl trimethoxysilane, 3-(N-allylamino) propyltrimethoxysilane, or a combination of two or more thereof.

In one embodiment, the organic radical polymerizable monomers (b) are selected from hydrophilic monomers such as N,N-dimethylacrylamide, N,N-,dimethylmethacrylamide, N-vinyl-2-pyrrolidone, 2-hydroxyethyl methacrylate, 2-hydroxy ethylacrylate, dimethylaminoethyl methacrylate, etc.

In yet another embodiment, the free radical polymerizable group (b) is selected from an organo-modified silicone. Non-limiting examples of suitable organo-modified silicones include silicone, having the general structures of Formulas 10-17:

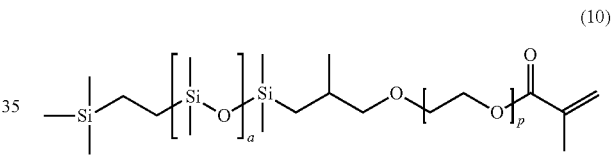

where p is 0 to 100, in one embodiment, 2 to 15, and a is 0 to 100, in one embodiment 0 to 20;

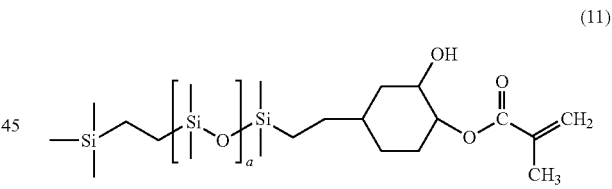

where a is 0 to 100, in one embodiment 0 to 20; the pre-polymer can contain one or mixture of all possible isomers;

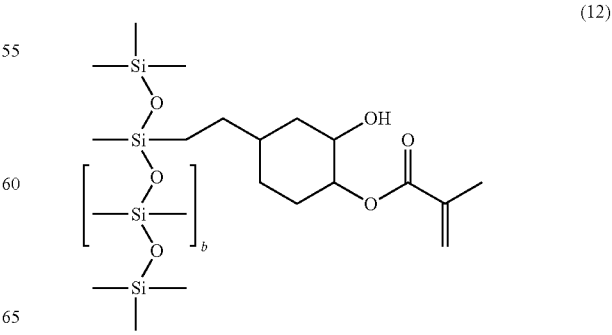

where b is 0 to 100, and in one embodiment, 0 to 20; the pre-polymer can contain one or mixture of all possible isomers;

(13)

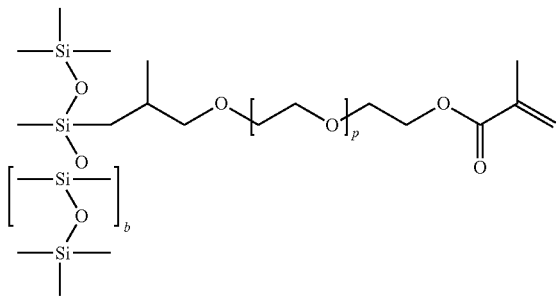

where p is from 1 to 50, in one embodiment 2 to 15, and b is 0 to 100, in one embodiment 0 to 20;

(14)

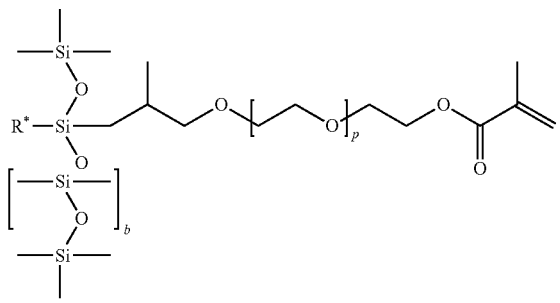

wherein, R* is a trialkylsilyloxy group or a methyl group, p is 1 to about 50, or from 2 to about 15, or even about 8, and b is 0 to about 100, or from 0 to 2 inclusive, or even 0;

(15)

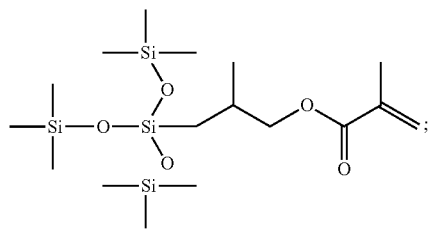

(16)

where R is a methyl radical, a is between 1 to 50, b is between 1 to 50; Z is a 2-methyl propyl started polyether moiety comprising —CH$_2$CH$_2$O—, —CH$_2$CH(CH$_3$)O—, —CH$_2$CH$_2$CH$_2$O— and their analogues with up to 6 carbon atoms capped with methacryl group; and (17)

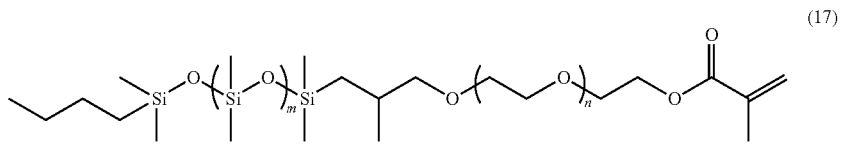

where m is 1 to 100, in one embodiment 1 to 50, and n is 0 to 50, in one embodiment 0 to 20.

The ratio of the silicone pre-polymer to the other hydrophilic unsaturated organic monomers is, in one embodiment from 1:100 to about 100:1; about 1:75 to about 75:1; from about 1:50 to about 50:1; from about 1:25 to about 25:1; from about 10:1 to about 1:10; from about 1:5 to about 5:1 even about 1:1. Monomers and polymers with linear alkyl linked (meth)acrylated silicone polyether chains means those compounds without any branching in the linking group that connects the siloxane with the polyalkylene oxide part of the side chain in such compounds. Notations such as (meth)acrylate denote monomer with either acrylate or methacrylate functionality. The monomers of the present invention can be used to obtain cured elastomers with desirable physical strength and resistance to tearing after absorption of water. The mono-(meth)acrylate functionalized silicone monomers/polymers of the present invention and their preparation and use in contact lens are further described in the sections below.

The initiator (c) for example, can be selected from materials known for such use in the polymerization art in order to promote and/or increase the rate of the polymerization reaction. An initiator is a chemical agent capable of initiating polymerization reactions. The initiator can be a photoinitiator or a thermal initiator.

A photoinitiator can initiate free radical polymerization and/or cross-linking by the use of light. Suitable photoinitiators, include, but are not limited to, benzoin methyl ether, diethoxyacetophenone, benzoylphosphine oxide, 2-hydroxy-2-methyl propiophenone (HMPP), 1-hydroxycyclohexyl phenyl ketone and Darocur and Irgacure types, preferably Darocur® 1173 and 2959. Examples of benzoylphosphine initiators include 2,4,6-trimethylbenzoyl-diphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators that can be incorporated, for example, into a macromer or can be used as a special monomer are also suitable. Examples of reactive photoinitiators include those disclosed in EP 632329, which is herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator are azobisisobutyronite (AIBN) and 1,1'-Azobis(cyclohexanecarbonitrile).

RAFT refers to reversible addition fragmentation chain transfer technique used in the polymerization. RAFT Reagent refers to a compound having the general formula,

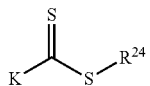

In which $R^{24}$ is a leaving group and K is an activating group. The terms used here have its traditional meanings as understood by skilled persons in the art. Any known RAFT reagents can be used in the invention for synthesizing pre-polymers, RAFT reagents belong to dithiobenzoates, trithiocarbonates, xanthates, and dithiocarbamates classes are considered in the RAFT reactions. The preferred reagent is 4-cyano-4-(phenylcarbonothioyltrio)pentanoic acid and 2-(Dodecylthiocarbonothioylthio)-2-methylpropionic acid in the context of present invention.

ATRP refers to atom transfer radical polymerization techniques, well known in the art, used in living radical polymerization. ATRP conditions involve the utilization of an initiator and a catalyst. ATRP initiators can be selected from any of the following class, halogenated alkanes, benzylic halides, alpha-haloesters, alpha-haloketone, alpha-halonitrile, or sulfonyl chloride. The ATRP catalyst is a metal ligand complex with metal part comprising of Mo, Cr, Re, Ru, Fe, Rh, Ni, Pd, Cu and a ligand. The ligand used can be a bidentate (e.g., 2,2'-bipyridine, N,N,N',N',-tetramethyl ethylenediamine), tridentate (e.g., N,N,N',N'',N''-pentamethyldiethylenetriamine (PMDETA)), or tetradentate (e.g., 1,1,4,7,10,10-hexamethyltriethylenetetramine, tris(2-(dimethylamino)ethyl)amine)). The preferred catalyst used in the present invention is Cu-PMDETA complex.

The cross-linking agent (d) can generally have two or more reactive functional groups at different sites of the molecule. Typically, these sites contain polymerizable olefinic unsaturation groups. During curing, they form a covalent bond with two different polymer chains and form a stable three-dimensional network to improve the strength of these polymer. Non-limiting examples of suitable cross-linking agents include acrylates, methacrylates, acrylamide, methacrylamide, thio, cyanurate, etc. Few examples that can be used but not limited to are ethylene glycol dimethacrylate, 1,6-hexanediol diacrylate, diethylene glycol dimethacrylate, pentaerythritol tetramethacrylate, glycerol dimethacrylate, triallyl cyanurate, ethylenediamine dimethacrylamide, bisphenol A dimethacrylate, coatosil, diacrylate or dimethacrylate terminated polydisiloxanes, diacrylamide terminated polydimethyl siloxanes, dimethacrylamide terminated polydimethylsiloxanes, dimethacrylated polyether modified polydimethylsiloxanes, Cross-linking agents conventionally used in contact lenses include ethylene glycol dimethacrylate and trimethyloylpropane trimethacrylate (about 0.1 to 2 wt. %). Other useful cross-linking agents include diethyleneglycol dimethacrylate, bisphenol A dimethacrylate, diglycidyl bisphenol A dimethacrylate and dimethacrylate-terminated polyethylene glycol and reactive linear polyether modified silicones.

The polymers and hydrogel of this invention may also contain ultraviolet absorbents, pigments and colorants in the form of additives or co-monomers.

The present invention also provides silicone-hydrogel compositions comprising (meth)acrylate functionalized hydrophilic silicone monomer and conventional monomer such as HEMA or other contact lens monomers to produce soft, flexible water absorbing films. The polymers of the present invention can absorb about 10 wt. % to about 60 wt. % of water, showing excellent surface wettability and effective oxygen permeability, all of which are necessary for the better comfort when lens are worn and for good health of the human cornea. The present invention also provides contact lenses made from the silicone-hydrogel films of the claimed invention. These embodiments are further described below.

To form polymers or hydrogel composition of the present invention, the desired the silicone pre-polymer and monomers are mixed and the resulting mixture is polymerized and cured to form transparent thin films by known thermal or UV cure techniques, using either peroxides or photoinitiators in the presence of cross-linking agents.

The hydrogel compositions of the current invention may be used to form hydrophilic silicone homo/copolymers that produce silicone-hydrogel films having better oxygen permeability and significantly improved surface wettability in comparison to monomers with linear alkyl linking groups in the polyether chains. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable and exhibit high oxygen permeability.

The polymers of the present invention form a clear, transparent homogeneous single-phase solution that can be cured directly without employing any additional homogenizing solvents, depending on the molecular weight of the present siloxane monomers, which are miscible with hydrophilic hydrogel monomers. Calculated solubility parameter values based on Fedors method (Robert F. Fedors, *Polymer Engineering and Science*, February 1974, vol. 14, No. 2) for the present inventive monomers range from approximately 16.5 to approximately 19 $(J/mol)^{1/2}$, which is closer to the solubility parameter value of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.7 $(J/mol)^{1/2}$.

In another embodiment of the present invention, the polymers may be formed into silicone-hydrogel films, via. processes known in the art. The silicone-hydrogel films of the present invention are soft, flexible and highly transparent. Silicone-hydrogel films made from the inventive monomers exhibit better surface wettability and oxygen permeability compared to ones made using monomers having linear alkyl linked methacrylated silicone polyether chains. The oxygen permeability of the hydrogel films or lenses can be from 40 Dk to 400 Dk units by selecting the silicone pre-polymers, independently or in combinations, of the present invention. The present silicone hydrogel films were found to have dynamic advancing contact angles with water, in the range of 100° to 20° and absorb about 10 to 70 wt. % of water, which can vary depending on the molecular weight of the polyethers. The contact angle can also be altered in the defined range by adding wetting agents like poly(vinyl pyrrolidone), or poly(vinyl alcohol). The silicone hydrogels also have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of solvent, as they are incompatible with each other. However in the current invention, the inventive hydrophilic silicone macromers are found to be miscible with conventional hydrophilic hydrogel monomers (such as HEMA, NVP and DMA) and can form a homogeneous solution suitable to produce silicone-hydrogel films without employing any solvent.

The densities of the present monomers generally range from 0.89-1.1 g/cm$^3$ at 25° C. and the refractive index range from 1.4-1.46 for the sodium D line. The instant inventors have found that monomers with refractive index greater than 1.431 and density greater than 0.96 g/cm$^3$ produce completely miscible compositions or pseudo miscible compositions that appear homogeneous, clear and transparent with hydrophilic monomers like HEMA, in the absence of compatibilizing solvents. As has been stated above, conventional silicone monomers (for example, TRIS) must be mixed with hydrophilic monomers like HEMA in the presence of a solvent to get miscible compositions to make silicone hydrogels. The hydrogel co-monomer used to make silicone-hydrogel copolymers of the present invention can be hydrophilic acrylic monomers such as HEMA, N,N-Dimethylacrylamide (DMA), N-Vinylpyrrolidone (NVP), Methacrylic acid (MAA) etc.

In the present invention, the resulting polymers may be formed into silicone-hydrogel films, via. processes known in the art. Accordingly, the present invention is also directed to contact lens produced from either homo or copolymers of the present invention. The monomers/polymers of the present invention can be formed into contact lenses by spin casting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates, tubes or rods, which may then be processed (e.g., cut or polished via. lathe or laser) to give a contact lens having a desired shape.

The relative softness or hardness of the contact lenses fabricated from the resulting polymer of this invention can be varied by decreasing or increasing the molecular weight of the polysiloxane pre-polymer end-capped with the activated unsaturated group (such as methacryloxy) or by varying the percent of the co-monomer. Generally, as the ratio of polysiloxane units to end-cap units increases, the softness of the material increases.

As stated above, the silicone-hydrogels of the present invention exhibit higher oxygen transport with improved surface wettable properties when compared to silicone-polyether copolymers having linear alkyl linking groups. The monomers and pre-polymers employed in accordance with this invention are readily polymerized to form three-dimensional networks, which permit the transport of oxygen with improved wettability along with better mechanicals and optical clarity.

Specific use of the films include intraocular contact lenses, artificial corneas, and soft disposable long-wear contact lenses or as coatings for biomedical devices.

Other Applications

Apart from being suitable to form hydrogel compositions for use in making films for contact lens applications, the present compositions can also be used in a variety of applications. In one aspect the composition comprises homo or copolymers prepared in bulk or latex form. These homopolymer, copolymer, emulsion, and latex particles comprising the macromer of current invention can be used as ingredients in personal care formulations including skin care, hair care, and nail care, such as lipsticks, mascaras, foundations, lotions, creams, shampoos, conditioners, and nail polishes, to improve their ware, tactile properties and ease of application. They also can be used in textile and fiber treatment applications to impart smooth, soft feel and wettability to both natural and synthetic fibers. Finally the homopolymer, copolymer, emulsion and latex particles can be incorporated into coating formulations for metal, plastic, wood and paper, such as varnishes, latex paints, and roofing compositions.

In one embodiment, the composition can be employed in a personal care composition as film formers. Examples of personal care compositions in which the composition can be utilized include, but are not limited to, deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin, combinations of two or more thereof, etc.

It will be appreciated that the compositions in which the compositions of the present inventions are employed may include other ingredients and components as desired for a particular purpose or intended use. For example, personal care compositions may include ingredients chosen from emollient, moisturizer, humectant, pigment, coated mica, colorant, fragrance, biocide, preservative, antioxidant, antimicrobial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, surfactants, emulsifiers, solvents, emollients, moisturizers, humectants, pigments, colorants, fragrances, biocides, preservatives, chelating agents, antioxidants, antimicrobial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, film formers, thickening agents, particulate fillers, silicones, clays, plasticizers, humectants, occlusive, sensory enhancers, esters, resins, film formers, film forming emulsifiers, high refractive index materials, combinations of two or more thereof, etc.

In another embodiment, the compositions may be utilized as film formers in an agricultural composition such as, for example, a fertilizer, a pesticide, etc.

In still another embodiment, the compositions can be employed in a component in adhesive formulations.

Aspects of the invention may be further understood with reference to the following non-limiting examples.

EXAMPLES

Hydrophilic Silicone Monomers

Example 1

Methacrylated poly(trisiloxanepolyether)$_8$ via ATRP

A silicone polyether monomer with a terminal methacrylate group with the average structure $((CH_3)_3SiO)_2Si(CH_3)CH_2CH(CH_3)CH_2O(CH_2CH_2O)_8C(O)C(CH_3)CH_2$ was homopolymerized to the target degree of polymerization ($D_p$) of 8 via ATRP using 2-hydroxyethyl 2-bromoisobutyrate. A calculated amount of silicone polyether and toluene were charged into a round bottom flask equipped with a condenser, and rubber septum. The reaction mixture was purged by bubbling nitrogen directly into the mixture via. a Hamilton needle. A required amount of PMDETA and Cu(I)Br were added, and the reaction mixture was further purged. The mixture turned to mint green color, which indicates formation of a Cu-PMDETA complex. Finally, 2-hydroxyethyl 2-bromoisobutyrate was added to the mixture, and the flask is placed in an oil bath maintained at 70° C. The mole ratio of ligand/initiator/catalyst was maintained at 1/1/1. The reaction was quenched by adding hexane to the mixture. The Cu salts were filtered out and the solvents were removed to yield blue colored viscous product. The product is re-dissolved in acetone and stirred over Tulsion T-66 MP (Tulsion from Thermax India Ltd.) to remove any copper traces. Removal of solvents yields a pale yellow viscous product hydroxy poly(trisiloxanepolyether)$_8$. A typical ATRP reaction leads to 80-95% conversion.

Hydroxy poly(trisiloxanepolyether)$_8$ was methacrylated to get the ethylenically-unsaturated terminal group. A round bottom flask equipped with a dropping funnel and a nitrogen inlet was charged with Hydroxy poly(trisiloxanepolyether)$_8$, toluene and triethylamine at ice bath temperature. A calculated amount of methacryloyl chloride was added drop wise for 20 minutes. The reaction was stirred at the same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid byproducts formed during the methacrylation. The product was filtered and 50 ppm hydroquinone was added to the filtrate. Removal of solvents yields a pale yellow color viscous liquid, methacrylated poly(trisiloxanepolyether)$_8$. All the reaction steps and products were confirmed by $^1H$ and $^{29}Si$ NMR's.

Example 2

Methacrylated poly(trisiloxanepolyether)$_3$ via FRP

A silicone polyether monomer with terminal methacrylate group with the average structure $((CH_3)_3SiO)_2Si(CH_3)CH_2CH(CH_3)CH_2O(CH_2CH_2O)_8C(O)C(CH_3)CH_2$ was homopolymerized to the target degree of polymerization ($D_p$) of 4 via. FRP using 2,2'-Azobis(2-methylpropionitrile) as initiator and mercaptoethanol as chain transfer agent (CTA). A calculated amount of silicone polyether and toluene were charged into a round bottom flask equipped with a condenser and rubber septum. The reaction mixture was purged by bubbling nitrogen directly into the mixture via. a Hamilton needle. A calculated amount of mercaptoethanol and 2-2'-azobis(2-methylpropionitrile) were added to the reaction mixture and the mixture was purged further. The flask was placed in an oil bath maintained at 70-75° C. The reaction was quenched after adding hexane to the reaction mixture. Removal of solvents yields a pale yellow colored viscous product hydroxy poly(trisiloxanepolyether)$_3$. A typical FRP reaction goes up to 80-90% conversion.

Hydroxy poly(trisiloxanepolyether)$_3$ was methacrylated to get the ethylenically-unsaturated terminal group. A round bottom flask equipped with a dropping funnel and nitrogen inlet was charged with Hydroxy poly(trisiloxanepolyether)$_3$, toluene and triethylamine and was placed in an ice bath. A calculated amount of methacryloyl chloride was added drop wise. The reaction was stirred at the same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid byproducts formed during the reaction. The product was filtered and 50 ppm Hydroquinone was added to the filtrate. Removal of solvents yields a pale yellow colored viscous liquid, methacrylated poly(trisiloxanepolyether)$_3$. All the reaction steps and products were confirmed by $^1$H and $^{29}$Si NMR's.

Example 3

Methacrylate functionalized P(trisiloxanepolyether-ran-HEMA)

A silicone polyether monomer with terminal methacrylate group with the average structure $((CH_3)_3SiO)_2Si(CH_3)CH_2CH(CH_3)CH_2O(CH_2CH_2O)_8C(O)C(CH_3)CH_2$ was copolymerized with 2-hydroxyethyl methacrylate (HEMA) to the total degree of polymerization ($D_p$) of 6 via FRP using 2-2'-Azobis(2-methylpropionitrile) as initiator and Mercaptoethanol as chain transfer agent (CTA). A calculated amount of silicone polyether, HEMA, toluene and 2'-azobis(2-methylpropionitrile) were charged into a round bottom flask equipped with a condenser and rubber septum. The reaction mixture was purged by bubbling nitrogen directly into the mixture via. a Hamilton needle. A calculated amount of 2-mercaptoethanol were added to the reaction mixture and the flask was placed further in an oil bath maintained at 70-75° C. The reaction was quenched after adding hexane to the reaction mixture. Removal of solvents yields a pale yellow colored viscous product OH—P(trisiloxanepolyether-ran-HEMA)$_5$. Typical FRP reaction goes to near 80% conversion.

The OH—P(trisiloxanepolyether-ran-HEMA)$_5$ was methacrylated further to get the ethylenically-unsaturated terminal group. A round bottom flask equipped with a dropping funnel and a nitrogen inlet was charged with OH—P(trisiloxanepolyether-ran-HEMA)$_5$, toluene and triethylamine at ice bath temperature. A calculated amount of methacryloyl chloride was added drop wise. The reaction was stirred at the same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid byproducts formed during the reaction. The product was filtered and 50 ppm hydroquinone was added to the filtrate. Removal of solvents yields a pale yellow colored viscous liquid, Mac-P(trisiloxanepolyether-ran-HEMA))$_5$. All the reaction steps and products were confirmed by $^1$H and $^{29}$Si NMR's.

Example 4

Methacrylate functionalized P(trisiloxanepolyether-ran-NVP)

A silicone polyether monomer with terminal methacrylate group with the average structure $[C_{31}H_{66}O_{12}Si_3]$ was copolymerized with N-vinylpyrrolidone (NVP) to the total degree of polymerization ($D_p$) of 6 via FRP using 2-2'-Azobis(2-methylpropionitrile as initiator and mercaptoethanol as chain transfer agent (CTA). A calculated amount of silicone polyether, NVP, toluene and 2'-azobis(2-methylpropionitrile) were charged into a round bottom flask equipped with a condenser and a rubber septum. The reaction mixture was purged by bubbling nitrogen directly into the mixture via. a Hamilton needle. A calculated amount of 2-Mercaptoethanol were added to the reaction mixture and the flask was placed further in an oil bath maintained at 70-75° C. The reaction was quenched after adding hexane to the reaction mixture. Removal of solvents yields a pale yellow colored viscous product OH—P(trisiloxanepolyether-ran-NVP)$_5$. A typical FRP reaction goes to near 80% conversion.

The OH—P(trisiloxanepolyether-ran-NVP)$_5$ was methacrylated further to get the ethylenically-unsaturated terminal group. A round bottom flask equipped with a dropping funnel and a nitrogen inlet was charged with OH—P(trisiloxanepolyether-ran-NVP)$_5$, toluene and triethylamine at ice bath temperature. A calculated amount of methacryloyl chloride was added drop wise. The reaction was stirred at same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid byproducts formed during the reaction. The product was filtered and 50 ppm Hydroquinone was added to the filtrate. Removal of solvents yields a pale yellow color viscous liquid, Mac-P(trisiloxanepolyether-ran-NVP))$_5$. All the reaction steps and products were confirmed by $^1$H and $^{29}$Si NMR's.

Example 5

Methacrylate functionalized P(trisiloxanepolyether-ran-DMA)

A silicone polyether monomer with the average structure $((CH_3)_3SiO)_2Si(CH_3)CH_2CH(CH_3)CH_2O(CH_2CH_2O)_5C(O)C(CH_3)CH_2$ was copolymerized with N,N-dimethylacrylamide (DMA) to the total degree of polymerization ($D_p$) of 10 via FRP using 1,1'-azobis(cyclohexanecarbonitrile) initiator and mercaptoethanol as chain transfer agent (CTA). A calculated amount of silicone polyether, DMA, toluene and 1,1'-azobis(cyclohexanecarbonitrile) were charged into a round bottom flask equipped with a condenser and a rubber septum. The reaction mixture was purged by bubbling nitrogen directly into the mixture via. a Hamilton needle. A calculated amount of 2-mercaptoethanol were added to the reaction mixture and the flask was placed further in an oil bath maintained at 95° C. The reaction was quenched after adding hexane to the reaction mixture. Removal of solvents yields a pale yellow viscous product OH—P(trisiloxanepolyether-ran-DMA)$_{10}$. The reaction went to about 95% conversion.

The OH—P(trisiloxanepolyether-ran-DMA)$_{10}$ was methacrylated to get the ethylenically-unsaturated terminal group. A round bottom flask equipped with a dropping funnel and a nitrogen inlet was charged with OH—P(trisiloxanepolyether-ran-DMA)$_{10}$, toluene and triethylamine and was placed in ice bath. A calculated amount of methacryloyl chloride was added drop wise. The reaction was stirred at the same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid formed during the reaction. The product was filtered and 50 ppm Hydroquinone was added to the filtrate. Removal of solvents yields a pale yellow colored viscous liquid, Mac-P(trisiloxanepolyether-ran-DMA))$_{10}$. All the reaction steps and products were confirmed by $^1$H and $^{29}$Si NMR's.

Example 6

Methacrylate functionalized P[5-(2-(1,1,1,3,5,5,5-heptamethyltrisiloxane-3-yl)ethyl)-2-hydroxycyclohexylacrylate]

5-(2-(1,1,1,3,5,5,5-heptamethyltrisiloxane-3-yl)ethyl)-2-hydroxycyclohexylacrylate) was homopolymerized to the target degree of polymerization ($D_p$) of 10 via FRP using 1,1'-azobis(cyclohexanecarbonitrile) initiator and mercaptoethanol as chain transfer agent (CTA). A calculated amount of silicone monomer, toluene and 1,1'-Azobis(cyclohexanecarbonitrile) were charged into a round bottom flask equipped with a condenser and a rubber septum. The reaction mixture was purged by bubbling nitrogen directly into the mixture via. a Hamilton needle. A calculated amount of 2-mercaptoethanol were added to the reaction mixture and the flask was placed further in oil bath maintained at 95° C. The reaction was quenched after adding some hexane to the reaction mixture. Removal of solvents yields a pale yellow colored viscous product OH—P(5-(2-(1,1,1,3,5,5,5-heptamethyltrisiloxane-3-yl)ethyl)-2-hydroxycyclohexylacrylate))$_{10}$. The reaction went to about 95% conversion.

The hydroxyl group of OH—P(5-(2-(1,1,1,3,5,5,5-heptamethyltrisiloxane-3-yl)ethyl)-2-hydroxycyclohexylacrylate))$_{10}$ was methacrylated to get the ethylenically-unsaturated terminal group. A round bottom flask equipped with a dropping funnel and nitrogen inlet was charged with OH—P(5-(2-(1,1,1,3,5,5,5-heptamethyltrisiloxane-3-yl)ethyl)-2-hydroxycyclohexylacrylate))$_{10}$, toluene and triethylamine at ice bath temperature. A calculated amount of methacryloyl chloride was added drop wise. The reaction was stirred at same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid byproducts formed during the reaction. The product was filtered and 50 ppm hydroquinone was added to the filtrate. Removal of solvents yields a pale yellow colored viscous liquid, mac-P(5-(2-(1,1,1,3,5,5,5-heptamethyltrisiloxane-3-yl)ethyl)-2-hydroxycyclohexylacrylate))$_{10}$. All the reaction steps and products were confirmed by $^1$H and $^{29}$Si NMR's.

Example 7

Methacrylate functionalized P(5-(2-(1,1,1,3,5,5,5-heptamethyltrisiloxane-3-yl)ethyl)-2-hydroxycyclohexylacrylate-ran-DMA)

5-(2-(1,1,1,3,5,5,5-heptamethyltrisiloxane-3-yl)ethyl)-2-hydroxycyclohexylacrylate) was copolymerized with dimethyl acrylamide to the total degree of polymerization ($D_p$) of 10 via FRP using 1,1'-azobis(cyclohexanecarbonitrile) initiator and mercaptoethanol as chain transfer agent (CTA). A calculated amount of silicone monomer with the average structure [C$_{18}$H$_{38}$O$_5$Si$_3$], toluene and 1,1'-azobis(cyclohexanecarbonitrile) were charged into a round bottom flask equipped with a condenser and rubber septum. The reaction mixture was purged by bubbling nitrogen directly into the mixture via. a Hamilton needle. A calculated amount of 2-mercaptoethanol were added to the reaction mixture and the flask was placed further in oil bath maintained at 95° C. The reaction was quenched after adding hexane to the reaction mixture. Removal of solvents yields a pale yellow colored viscous product OH—P(5-(2-(1,1,1,3,5,5,5-heptamethyltrisiloxane-3-yl)ethyl)-2-hydroxycyclohexylacrylate)-ran-DMA)$_{10}$. The reaction went to about 95% conversion.

The hydroxyl group of OH—P(5-(2-(1,1,1,3,5,5,5-heptamethyltrisiloxane-3-yl)ethyl)-2-hydroxycyclohexylacrylate)-ran-DMA)$_{10}$ was methacrylated further to get the ethylenically-unsaturated terminal group. A round bottom flask equipped with a dropping funnel and nitrogen inlet was charged with OH—P(5-(2-(1,1,1,3,5,5,5-heptamethyltrisiloxane-3-yl)ethyl)-2-hydroxycyclohexylacrylate)-ran-DMA)$_{10}$, toluene and triethylamine at ice bath temperature. A calculated amount of methacryloyl chloride was added drop wise. The reaction was stirred at the same temperature for one hour and then at room temperature for 2 hours. The triethylamine hydrochloride salt formed was filtered out and the reaction mixture was concentrated. The product was re-dissolved in hexane and stirred over Tulsion A-2X MP (Tulsion from Thermax India Ltd.) to remove any methacrylic acid byproducts formed during the reaction. The product was filtered and 50 ppm Hydroquinone was added to the filtrate. Removal of solvents yields a pale yellow color viscous liquid, mac-P(5-(2-(1,1,1,3,5,5,5-heptamethyltrisiloxane-3-yl)ethyl)-2-hydroxycyclohexylacrylate)-ran-DMA)$_{10}$. All the reaction steps and products were confirmed by $^1$H and $^{29}$Si NMR's.

Example 8

Hydroxyl functionalized P(LA-ran-BA-ran-5-(2-(1,1,1,3,5,5,5-heptamethyltrisiloxane-3-yl)ethyl)-2-hydroxycyclohexylacrylate))

5-(2-(1,1,1,3,5,5,5-heptamethyltrisiloxane-3-yl)ethyl)-2-hydroxycyclohexylacrylate) was copolymerized with Lauryl acrylate and Butyl acrylate to the total degree of polymerization ($D_p$) of 180 via FRP using 1,1'-azobis(cyclohexanecarbonitrile) initiator and mercaptoethanol as chain transfer agent (CTA). Silicone monomer, Lauryl and butyl acrylate in required feed ratio were charged into round bottom flask along with toluene and 1,1'-azobis(cyclohexanecarbonitrile) The reaction mixture was purged by bubbling nitrogen directly into the mixture via a Hamilton needle. A calculated amount of 2-Mercaptoethanol were added to the reaction mixture and the flask was placed further in oil bath maintained at 95° C. The reaction was quenched after adding some hexane to the reaction mixture. Removal of solvents yields a pale yellow colored viscous product OH—P(LA-ran-BA-ran-5-(2-(1,1,1,3,5,5,5-heptamethyltrisiloxane-3-yl)ethyl)-2-hydroxycyclohexylacrylate)). The reaction went to about 95% conversion. The reaction was monitored and product was confirmed by $^1$H and $^{13}$C NMR's.

Example 9

Copolymer of 5-(2-(1,1,1,3,5,5,5-heptamethyltrisiloxane-3-yl)ethyl)-2-hydroxycyclohexylacrylate) and Butyl acrylate via. Emulsion polymerization 5-(2-(1,1,1,3,5,5,5-heptamethyltrisiloxane-3-yl)ethyl)-2-hydroxycyclohexylacrylate) (13 wt. %), Butyl acrylate (10 wt. %) and ethylene glycol dimethacrylate, EGDMA (0.25 wt. % of organic phase) were mixed thoroughly in an Erlenmeyer flask. This organic mixture was added drop wise to solution of sodium lauryl ether sulphate (5 wt. %) and water (72 wt. %) under vigorous stirring. To this emulsion, potassium persulfate (1 wt. % with respect to organic phase) was added as thermal initiator and the reaction was placed in oil bath maintained at 85° C. for 2 hours. The reaction went to 86% conversion with final solid content measuring to 24% while the expected was 28% respectively. The solution was poured onto a petridish for the water to evaporate to yield uniform film.

Hydrogel Films

Hydrogel films are prepared incorporating the materials from above examples along with other organic monomers such as 2-hydroxyethyl methacrylate (HEMA), N,N-dimethyl acrylamide (DMA), N-vinylpyrrolidone (NVP) and cross-linkers such as ethyleneglycol dimethacrylate (EGDMA). The films were cured using 2-hydroxy-2-methyl propiophenone or Irgacure 819 as radical initiators (0.5-1 wt. %). The resultant clear, homogeneous solution is poured into either glass, polypropylene, or PET (poly(ethylene terephthalate)) to a measuring gap of about 1 mm. The formulations are cured by exposure to 365 nm UV irradiation of intensity 105 mW/cm² for 5-40 seconds.

Table listing clear hydrogel formulations and their properties

| Components (wt. %) | Film 1 | Film 2 | Film 3 | Film 4 | Film 5 |
|---|---|---|---|---|---|
| Example 1 | 49.5 | | | | |
| Example 2 | | 49.5 | | | |
| Example 5 | | | 69.3 | | |
| Example 6 | | | | 49.5 | |
| Example 7 | | | | | 79.2 |
| HEMA | 19.8 | 19.8 | | | |
| NVP | 24.8 | 24.8 | | | |
| DMA | 4.9 | 4.9 | 29.7 | 49.5 | 19.8 |
| EGDMA | 0.49 | 0.49 | 0.49 | 0.49 | 0.49 |
| UV Initiator | 0.49 | 0.49 | 0.49 | 0.49 | 0.49 |
| % Water content | 52 | 45 | 28 | 47 | 30 |

While the invention has been described with reference to various embodiments, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A hydrogel composition comprising a siloxane prepolymer of the formula:

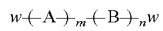

where m is a positive integer from 2 to about 100, and n is a positive integer from 0 to about 100; A is a divalent block having a formula:

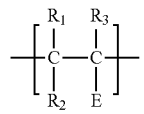

where, $R_1$, $R_2$, and $R_3$ are independently selected from hydrogen and a monovalent radical with 1 to 50 carbon atoms optionally containing one or more heteroatoms; E is a mono-valent group having a general structure of F-L-G, where F is a divalent linkage selected from an alkyl, an ester, an ether, an amine, an amide, a carbonate, and a carbamate; L is a divalent moiety chosen from a substituted or unsubstituted, linear, branched, cyclic, aliphatic, or aromatic hydrocarbon of 1-100 carbon atom optionally containing one or more heteroatoms; and G is a siloxane unit having the general structure $M^1_a M^2_b D^1_c D^2_d T^1_e T^2_f Q_g$, where, $M^1 = R_5 R_6 R_7 SiZ_{1/2}$, $M^2 = R_8 R_9 R_{10} SiZ_{1/2}$, $D^1 = R_{11} R_{12} SiZ_{2/2}$, $D^2 = R_{13} R_{14} SiZ_{2/2}$, $T^1 = R_{15} SiZ_{3/2}$, $T^2 = R_{16} SiZ_{3/2}$, $Q = SiZ_{4/2}$; $R_5$, $R_6$, $R_7$, $R_9$, $R_{10}$, $R_{11}$, $R_{12}$, $R_{14}$, and $R_{15}$ are independently chosen from a monovalent hydrocarbon radical having 1 to about 50 carbon atoms optionally containing one or more heteroatoms; $R_8$, $R_{13}$, and $R_{16}$ are independently selected from a divalent residue of a non-isomerizable hydrosilylation effective terminal olefin having a structure:

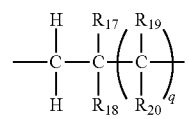

where, $R_{18}$, $R_{19}$, and $R_{20}$ are independently selected from hydrogen and a hydrocarbon radical with 1 to 10 carbon atoms optionally containing one or more heteroatoms, the integer q is 0 to 10, and $R_{17}$ is a hydrocarbon radical with 1 to 5 carbon atoms or a hydrogen atom such that $R_{17}$ is hydrogen when q=0 and L is a cyclic residue; a, c, e, and g are zero or a positive integer such that 0<a+b+c+d+e+f+g<500; subscripts b, d, and f have values of 0 or 1 such that b+d+f=1; and Z is chosen from O or a $CH_2$ group subject to the limitation that the molecule contains an even number of $O_{1/2}$ and an even number of $(CH_2)_{1/2}$ groups, and the $O_{1/2}$ and the $(CH_2)_{1/2}$ groups both are all paired in the molecule;

B is a divalent radical having a formula:

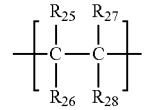

where $R_{25}$, $R_{26}$, $R_{27}$, and $R_{28}$ are independently selected from hydrogen, a halogen, hydroxyl, and a hydrocarbon radical comprising aromatic, aliphatic, and/or aralkyl moieties optionally having heteroatoms; W includes at least one reactive group X and, optionally, a chain stopper group Y, wherein:

X is a free radical polymerizable group having a formula:

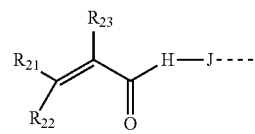

where $R_{21}$, $R_{22}$, and $R_{23}$ can be selected from hydrogen or a monovalent hydrocarbon radical with 1 to 5 carbon atoms, which may optionally contain one or more heteroatoms; H can be O or $NR_{24}$, where $R_{24}$ can be hydrogen or a monovalent hydrocarbon radical with 1-5 carbons; J is a divalent moiety chosen from a substituted or unsubstituted aliphatic or aromatic hydrocarbon having of 1-10 carbon atoms and may optionally contain one or more heteroatoms; and Y can be independently selected from hydrogen, hydroxyl, thiol, amine or a monovalent hydrocarbon radical having 1 to 10 carbon atoms, which may optionally contain one or more heteroatoms.

2. The pre-polymer in the composition of claim 1, wherein L is a hydrophilic residue chosen from a polyalkyleneoxide, optionally a polyalkyleneoxide chosen from —$CH_2CH_2O$—, —$CH_2CH(CH_3)O$—, —$CH_2CH_2CH_2O$—, and their analogues with up to 6 carbon atoms.

3. The pre-polymer in the composition of claim 1, wherein L is a cyclic hydrocarbon residue with the structure:

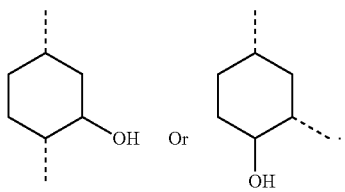

4. The pre-polymer in the composition of claim 1 wherein $R_9$, $R_{10}$, $R_{11}$, $R_{13}$, $R_{14}$, $R_{15}$, $R_{16}$, $R_{18}$, and $R_{20}$ in the unit G of group E are independently selected from a hydrocarbon radical chosen from methyl, ethyl, propyl, iso-propyl, butyl, isobutyl, phenyl, naphthyl, an aralkyl radical with 8 to 20 carbon atoms, trifluoromethylpropyl, and combinations of two or more thereof.

5. The pre-polymer in the composition of claim 1, wherein the mono-functional group E has a structure chosen from any of the formulas:

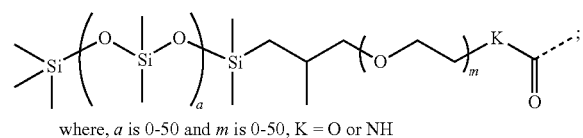

where, $a$ is 0-50 and $m$ is 0-50, K = O or NH

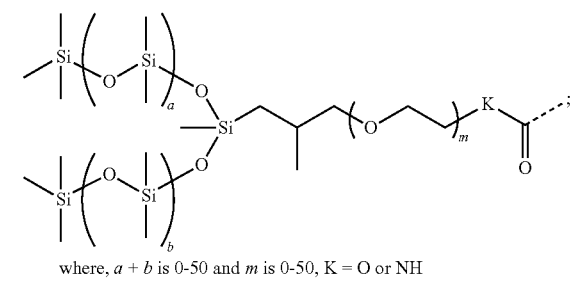

where, $a + b$ is 0-50 and $m$ is 0-50, K = O or NH

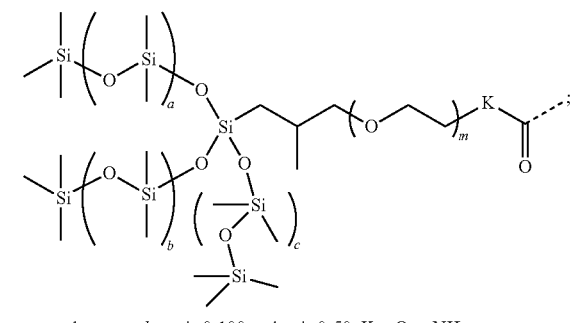

where, $a + b + c$ is 0-100 and $m$ is 0-50, K = O or NH

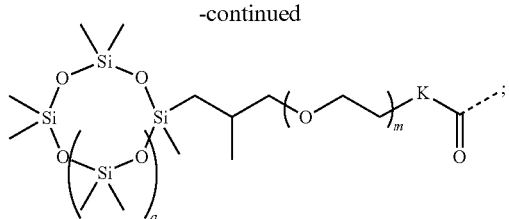

where, $a$ is 1-50 and $m$ is 0-50, K = O or NH

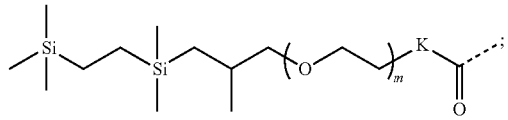

where $m$ is 0-50, K = O or NH

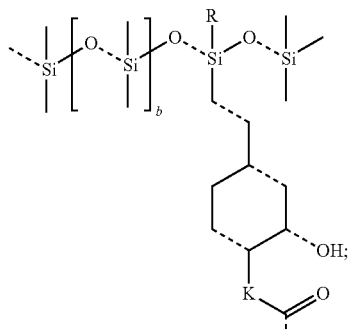

where K is O or NH, R is —$CH_3$ or —$(OSi(CH_3)_2)_n$, $b$ is 0-100, and $n + b$ is 0-100

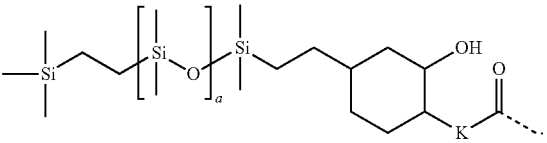

where K is O or NH, and $a$ is 0-100

6. The pre-polymer in the composition of claim 1, where $R_{25}$ and $R_{26}$ are hydrogen, $R_{27}$ is chosen from hydrogen or a methyl radical, and $R_{28}$ is a part of an ethylenically-unsaturated hydrophilic monomer or a hydrophobic monomer.

7. The composition of claim 1, wherein the siloxane pre-polymer has at least one terminal reactive group.

8. The composition of claim 1 where the siloxane pre-polymer is (a) a homopolymer or (b) a copolymer.

9. The composition of claim 8, wherein the pre-polymer is a copolymer further comprising a free-radical polymerizable organic monomer chosen from a vinylic monomer, an acrylide monomer, an acrylic monomer, or a combination of two or more thereof.

10. The copolymer of claim 8, wherein the vinylic monomer is chosen from N-vinyl-pyrrolidone, N-vinyl-caprolactam, N-vinyl-acetamide, N-vinyl-formamide and N-vinyl-isopropylamide, vinyl benzene, vinyl naphthalene, vinyl pyridine, vinyl alcohol, vinyl containing silicones, or a combination of two or more thereof.

11. The copolymer of claim 8, wherein the acrylic monomers are chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-Dimethylacrylamide, N-isopropylacrylamide, acrylamide, methacrylamide, acrylic acid, methacrylic acid, acrylated hydrophilic or hydrophobic organo-silicones, or c combination of two or more thereof.

12. The copolymer of claim 8 optionally comprises a cross-linker selected from ethylene glycol dimethacrylate, trimethyloylpropane trimethacrylate, diethyleneglycol dimethacrylate, bisphenol A dimethacrylate, diglycidyl bisphenol A dimethacrylate and dimethacrylate-terminated polyethylene glycol and reactive linear or pendant polyether modified silicones.

13. The composition of claim 1, wherein the initiator is a thermal or a photo initiator chosen from 2,2'-azobis (2,4-dimethylpentanenitrile), 2,2'-azobis (2-methylpropanenitrile), 2,2'-azobis (2-methylbutanenitrile), peroxides such as benzoyl peroxide, benzoin methyl ether, diethoxyacetophenone, a benzoylphosphine oxide, 2-hydroxy-2-methyl propiophenone (HMPP), 1-hydroxycyclohexyl phenyl ketone, an α-hydroxyketone type, a phenylglyoxylate type, a benysldimethyl-ketal type, an α-aminoketone type, a monoacyl phosphine type, a bis-acyl phosphine type, a phosphine oxide, a metallocene type, and an iodonium salt.

14. A contact lens comprising the hydrogel film of claim 1.

15. The contact lens according to claim 14 comprising a limited extraction protocol that further comprises a green or aqueous solvent chosen from water, an organic or inorganic salt solution, a buffer, an emulsion, a commercial lens cleaning solution, or an ophthalmically compatible solvent in the temperature range of 15-125° C. for extraction.

16. The hydrogel composition of claim 1, wherein the composition is a film forming additive in a textile, paper, leather, personal care, health care, home care, coating, painting, or seed treatment formulations.

* * * * *